United States Patent [19]

Fabry et al.

[11] Patent Number: 4,850,341
[45] Date of Patent: Jul. 25, 1989

[54] GLOVE FOR PROPHYLAXIS OF CARPAL TUNNEL SYNDROME

[76] Inventors: John J. Fabry, 226 Miramar Dr.; Bertram I. Milson, 3300 Miranda Ct., both of Green Bay, Wis. 54301

[21] Appl. No.: 40,441

[22] Filed: Apr. 16, 1987

[51] Int. Cl.$^4$ ................................................ A61H 7/00
[52] U.S. Cl. ........................................ 128/44; 128/77; 2/161 R
[58] Field of Search ............... 128/77, 87 A; 2/16, 2/20, 161 R, 161 A

[56] References Cited

U.S. PATENT DOCUMENTS

| D. 259,955 | 7/1981 | Helfersch | 128/77 |
|---|---|---|---|
| 1,377,103 | 5/1921 | Suhr | 2/16 |
| 1,667,926 | 5/1928 | Browsky | 2/20 |
| 3,327,703 | 6/1967 | Gamm | 128/77 |
| 3,896,498 | 7/1975 | Pang | 2/20 |
| 4,374,439 | 2/1983 | Norman | 2/161 A |
| 4,531,241 | 7/1985 | Berger | 2/161 R |
| 4,559,646 | 12/1985 | Ertl | 2/16 |
| 4,584,993 | 4/1986 | Nelson | 128/77 |
| 4,617,684 | 10/1986 | Green et al. | 2/19 |
| 4,651,350 | 3/1987 | Dawiedczyk | 2/161 R |

FOREIGN PATENT DOCUMENTS 220467 8/1924 United Kingdom ............... 2/161 R

OTHER PUBLICATIONS

Nissenbaum, et al., "Journal of Hand Surgery", Nov. 1980, pp. 544–547.
Excerpt entitled "Carpal Tunnel Exploration and Release", pp. 191–193.
Sebright, "Occupational Health and Safety", Sep. 1986, p. 18 et seq.
Rubatex, "Fabric Lined Wet Suit Materials", 2 pages.
"Rubatex Closed Cell Rubber and Vinyl Sheets", p. 107.
"Sorbethane: Solutions Materialized", 3 pages.
"The Vibration Isolation Effectiveness of 'Sorbethane', Mitts", 3 pages, 2 tables, 13 figures.
Saranac Catalog.

*Primary Examiner*—Edgar S. Burr
*Assistant Examiner*—Huong Q. Pham
*Attorney, Agent, or Firm*—Foley & Lardner

[57] ABSTRACT

A glove effective for preventing or inhibiting carpal tunnel syndrome has a pad disposed therein for protecting the median nerve of a wearer's hand. In a preferred embodiment the pad is secured to the glove body and extends from near the wrist opening of the glove to about the center of the portion of the glove which covers the palm. The pad is made of a resilient flexible material such as foam rubber which is effective to provide protection from vibrations and shocks. Such a glove is light-weight, allows considerable freedom for the fingers and wrist, yet protects the part of the hand between the ball of the thumb and the palm heel from the type of stress which can produce carpal tunnel syndrome.

19 Claims, 2 Drawing Sheets

GLOVE FOR PROPHYLAXIS OF CARPAL TUNNEL SYNDROME

TECHNICAL FIELD

This invention relates to a glove effective for prophylaxis of carpal tunnel syndrome by protecting the wearer's hand from strain which tends to cause carpal tunnel syndrome, particularly in persons whose occupation requires extended use of a manual implement.

BACKGROUND OF THE INVENTION

Carpal tunnel syndrome is a well known, commonly occurring hand condition, sometimes referred to as median compression neuropathy within the carpal canal. The most common symptoms of this condition include intermittent pain and numbness of the hand. Such pain or numbness results from compression of the median nerve which extends from the wrist centrally into the palm of the hand between the palm heel and the ball of the thumb (thenar). In carpal tunnel syndrome, a dense fibrous tissue called the transverse carpal ligament forms over the median nerve and compresses it, producing the symptoms of pain or numbness.

Treatment of carpal tunnel syndrome varies according to the severity of the condition. Severe conditions usually require hand surgery to sever the transverse carpal ligament. For less severe cases, the use of a splint which immobilizes the wrist is sometimes effective, often in combination with a anti-inflammatory medication. Such treatments are generally expensive, painful, and may reduce the patient's ability to use the affected hand during treatment.

Carpal tunnel syndrome is a particular problem for workers in industries which require repeated manual operations with a held implement or tool, such as a knife. In particular, workers in meat processing operations, the paper industry and the construction industry suffer from this problem, and carpal tunnel syndrome is a leading cause of workmen's compensation claims in such industries.

Protective gloves have been proposed as one means of preventing carpal tunnel syndrome due to wrist flexing in *Occupational Health and Safety*, September 1986, pages 18, 20. A glove proposed for this purpose in the foregoing publication includes a tough pigskin shell wrapped around the wearer's wrist. This glove is heavy, cumbersome, and restricts free action of the wrist.

The present invention provides a glove effective for inhibiting carpal tunnel syndrome by protecting the median nerve itself, rather than attempting to restrict wrist flexing.

SUMMARY OF THE INVENTION

The present invention provides a glove which has proven effective for inhibiting or preventing carpal tunnel syndrome because it has a pad configured to cover and protect the median nerve of a wearer's hand. According to one aspect of the invention, such a glove includes a glove body, preferably having a front and back which define therebetween a rear wrist opening, a front finger opening and a side thumb opening. A generally resilient, flexible, elongated pad is disposed on the front of the glove body. This pad extends forwardly from near the wrist to approximately the center of the front of the glove body, thereby covering the portion of the median nerve between the heel of the hand and the ball of the thumb. If an appropriate padding material is selected and configured, the glove according to the present invention can effectively protect the median nerve from compression resulting in carpal tunnel syndrome while allowing the wearer considerable freedom of action.

BRIEF DESCRIPTION OF THE DRAWING

The invention will be described with reference to the appended drawing, wherein like numerals denote like elements, and.

DETAILED DESCRIPTION OF A PREFERRED EXEMPLARY EMBODIMENT

Figure 1:
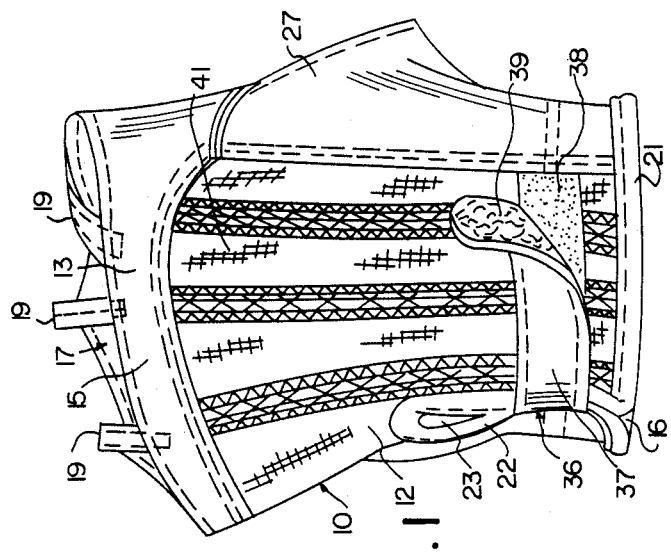
FIG. 1 is a rear plan view of a glove according to the invention.
Figure 2:
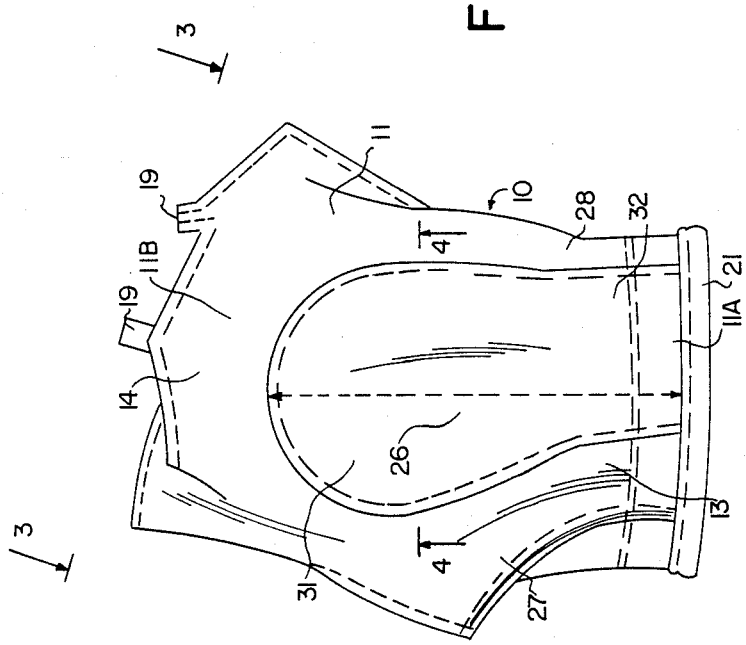
FIG. 2 is a front plan view of the glove shown in FIG. 1.
Figure 3:
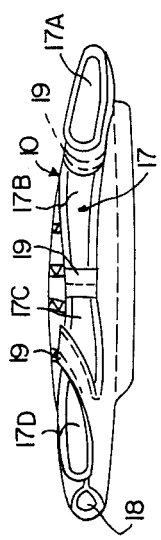
FIG. 3 is an view taken along the line 3—3 in FIG. 2.

FIGS. 1 through 3 illustrate a glove 10 according to the invention for preventing or inhibiting carpal tunnel syndrome. Glove 10 generally comprises a glove front 11 and glove back 12 sewn together in a face-to-face relationship to define a glove body 13. Glove front 11 and back 12 are configured and sewn together so as to define a rearwardly opening wrist opening 16, a frontwardly opening finger opening 17 and a side thumb opening 18. Front 11 includes a wrist portion 11A which adjoins a wearer's wrist and a palm covering portion 11B which overlies most or all of the wearer's palm.

Finger opening 17 is subdivided into four separate finger openings 17A, 17B, 17C, 17D by three loops 19 which are each attached at opposite ends thereof to a forward end portion 14 of glove front 11 and a forward end portion 15 of glove back 12, at spaced apart positions along finger opening 17. Glove body 13 also includes a generally lateral wrist cuff 21 of which wrist portion 11A is a part disposed along the rear edge of glove body 13, which cuff 21 has a forwardly extending portion 22 which defines a side vent 23 in glove body 13.

Figure 5:
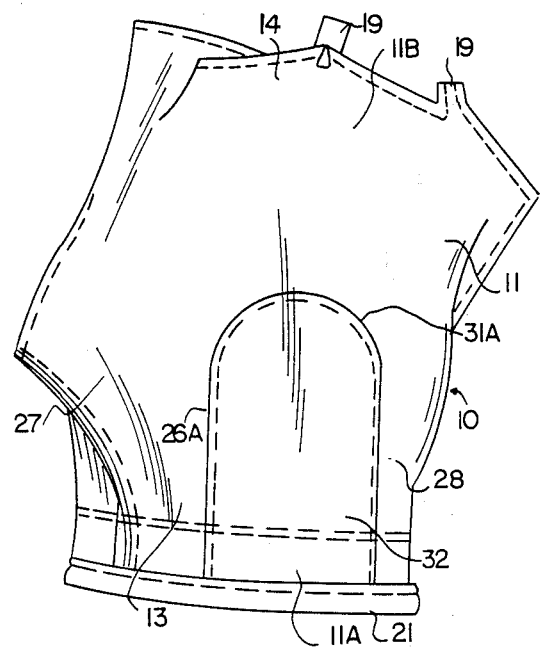
FIG. 5 is a front plan view of a glove according to an alternative embodiment of the invention.

A protective pad 26 is sewn to the inside of front 11 of glove body 13 between a thumb portion 27 which overlies the ball of the wearer's thumb and a palm heel portion 28 overlying the heel of the wearer's hand. Pad 26 extends forwardly from wrist cuff 21 to a position laterally aligned with at least the beginning of thumb opening 18, generally in close proximity to or covering the center of front 11 of glove body 13. The center of front 11 corresponds to the portion of front 11 which overlies the middle of the wearer's palm. In the illustrated embodiment, pad 26 has a forward end portion comprising a rounded, forwardly extending enlarged protuberance 31 and a less wide, rear end portion 32 adjoining wrist cuff 21. In an alternative embodiment shown in FIG. 5, a pad 26A is of generally rectangular shape, except that it has a semi-circular front end portion 31A that barely reaches the approximate center of front 11. This embodiment provides slightly less protection for the median nerve of the wearer's hand, but permits greater freedom for gripping a hand held object, i.e. greater flexibility in the palm. The characteristics and dimensions of pad 26 are important to providing a glove 10 effective for inhibiting carpal tunnel syndrome, as discussed in detail below.

Glove 10 preferably includes a releasable contact fastener 36 which acts as a means for selectively releasably securing glove 10 to the wearer's hand. Releasable fastener 36 includes a tab 37 attached to one edge of vent portion 22 and a base element 38 secured to glove body 13 on the side of side vent 23 opposite the side to which tab 37 is attached. In the illustrated embodiment, base element 38 comprises a piece of hook tape sewn to back 12, and the undersurface of tab 37 is made of fibrous pile material 39 so that releasable fastener 36 comprises a typical hook and loop closure. Releasable fastener 36 is located in close proximity to wrist cuff 21 to snugly secure glove 10 at the wearer's wrist.

Back 12 may include an elastic panel 41 extending from wrist cuff 21 over most of the length of back 12, i.e. near the wearer's knuckles and adjoining forward end portion 15. Elastic panel 41 provides a more secure fit for glove 10. Apart from elastic panel 1, the rest of glove body 13 is preferably made of a pliable, sturdy, inelastic material such as leather.

Figure 4:
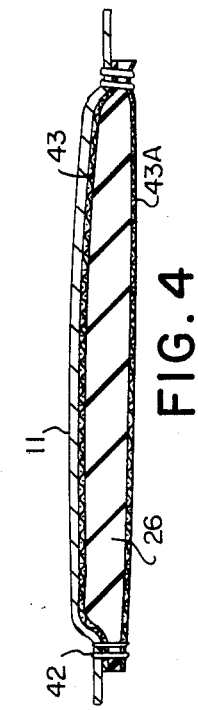
FIG. 4 is a cross-sectional view of the glove shown in FIG. 2 taken along the line 4—4 in FIG. 2.

As illustrated in FIG. 4, pad 26 is sewn to glove front 11 at a seam 42 disposed around the outer periphery of pad 26 between a pair of elastic fabric linings 43. Linings 43 hold pad 26 in place, and inner lining 43A provides a good feel to the inside of glove 10.

Glove 10 preferably lacks any type of finger or thumb coverings, other than loops 19. This provides the wearer with maximum freedom to perform tasks which require manual dexterity. This contrasts with typical sporting gloves, which have full fingers or short partial fingers, i.e. tubular finger or thumb coverings.

Pad 26 must have sufficient firmness to protect the palm of the hand along the median nerve from shocks or vibrations, but should have sufficient flexibility to permit the wearer to effectively grasp and use a hand tool while wearing the glove. Pad 26 is thus preferably made of an elastomeric material, such as foam rubber, particularly materials such as closed-cell neoprene, ethylene propylene terpolymer, (EPT), styrene butadiene (SBR), and similar elastomers. The following table sets forth the preferred properties of materials for use as pad 26:

| Property | Preferred Miminum | Preferred Range |
| --- | --- | --- |
| Compression Deflection, in p.s.i. | 2 | 5–9 |
| Durometer (Shore 00) | 25 | 40–60 |
| Density in p.c.f. | 5 | 12–20 |
| Resilience* | 25 | 30–55 |

*Bashore % rebound average, 0.5 inch thickness at 72° F.

Preferred pad materials include Rubatex (trademark of Rubatex Corp., Bedford, VA) R-421-N, R-422-N, R-427-N, R-425-N and Sorbothane (trademark of Sorbothane, Inc., Kent, OH).

Ordinary foam materials used as pads in conventional sporting gloves are generally too soft for use as pad 26. Thus, gloves for sports such as handball, wherein the palm is protected, are distinctly different from the glove 10 according to the present invention in both the size and shape of the protective pad and the characteristics of the pad. Pad 26 is most preferably made of a material having significant shock absorbing characteristics, so that shocks transmitted to the wrist by vibration or violent movement of the hand are dampened. The foregoing elastomeric materials are effective for this purpose.

Pad 26 has a preferred average width of at least about 4 cm, typically in the range from 4–10 cm, depending upon the size of the wearer's hand. Generally, the width of pad 26 is between one-half (0.5) and two-thirds (0.67) the width of wrist opening 16 when glove 10 is laid flat as illustrated in FIG. 2. The length L of pad 26 from its rearwardmost edge to its forwardmost edge, can vary considerably depending on both the size of the wearer's hand and the extent to which pad 26 overlies the wearer's palm. In general, length L should be at least about 5 cm, preferably in the range of from about 7 to 13 cm. Relative to the overall length of glove 10 from wrist cuff 21 to finger opening 17 (excluding any finger coverings), length L of pad 26 in the lengthwise direction of glove 10 is typically in the range of from about 50%–90% of the overall length of glove front 11, preferably in the range of about 60%–80% of the overall length of glove front 11.

The thickness of pad 26 is also important to providing sufficient protection for the hand. Thicknesses in the range of about 0.1 to 2 cm, particularly 0.5 to 1 cm, have been found advantageous because hand protection is provided without rendering the glove excessively bulky or inflexible.

A glove 10 according to the foregoing embodiment of the invention is effective for protecting the wearer from repeated shocks and vibrations which may cause carpal tunnel syndrome, yet is light-weight, permits the wearer's wrist and fingers to move freely, and can flex sufficiently to allow the wearer to grasp an implement such as a knife.

The foregoing embodiment of the invention was initially tested in a meat processing plant wherein workers cut meat with knives. In the plant which was the subject of the test, carpal tunnel syndrome was the main source of lost time and medical disability. Prior to providing workers with gloves according to the invention, the plant had nine cases of carpal tunnel syndrome requiring surgery over the course of the preceding year. One year after the use of gloves according to the present invention began, it was found that only one case of carpal tunnel syndrome had developed in that time period. In addition, a person diagnosed as having carpal tunnel syndrome in a mild form a few months prior to the use of the gloves according to the invention found that her symptoms gradually went away after using the gloves according to the invention for approximately ten months. These remarkable results illustrate the potential value of the present invention in the workplace.

It will be understood that the above description is of preferred exemplary embodiments of the invention, and that the invention is not limited to the specific forms shown. For example, the glove body could be limited to a series of straps attached to the pad for securing it on a wearer's hand. For users of heavier tools such as pneumatic hammers, it may be desirable to enlarge pad 26, or employ a stiffer material for pad 26, e.g. foam rubber having a compression deflection in the range of 9–13 psi. With appropriate modifications, e.g. including half or full finger coverings, the glove according to the invention is also useful in sports such as softball and racquetball wherein carpal tunnel problems can develop. These and other modifications may be made in the described invention without departing from the scope thereof as expressed in the appended claims.

We claim:

1. A glove effective for inhibiting carpal tunnel syndrome in the hand of the wearer who grasps and uses an implement with the hand on which said glove is worn, comprising:

a flexible glove body including a wrist cuff, and a glove front and back defining therebetween a rear wrist opening, a front finger opening subdivided into finger openings by a series of spaced-apart loops each attached at opposite ends thereof to said glove front and said glove back, and a side thumb opening, said glove front including a palm heel portion and a thumb portion, said wrist cuff configured for disposition about a wearer's wrist immediately adjacent the wearer's palm heel when said glove is worn by a wearer; and a flexible protective pad secured to said glove front between said palm heel portion and thumb portion, said pad being elongated in the lengthwise direction of said glove front, said pad having a thickness in the range of 0.2–2 cm, a length between 50% and 90% of the length of said glove front from said wrist cuff to said finger opening, and a width in the range of 0.5 to 0.67 of the width of said wrist cuff when said glove is laid flat, said pad having a tapered shape which converges toward said finger openings and said glove when worn by the wearer terminating at said wrist cuff immediately adjacent the wearer's palm heel, said pad being generally laterally aligned with said thumb opening and having a generally rectangular rear end portion adjoining said wrist cuff.

2. The glove of claim 1, wherein said pad is made of an elastomeric material having a compression deflection of at least 5 psi, a durometer of at least 40, a density of at least 5 pcf, and a resilient of at least about 25 based on a Bashore percent rebound average for 0.5 inch thickness at 72° F.

3. A glove effective for inhibiting carpal tunnel syndrome in the hand of a wearer who grasps and uses an implement with the hand on which the glove is worn, comprising:

a flexible glove body including a glove front having wrist cuff and a palm covering portion dimensioned such that, when said glove is disposed about a wearer's hand, said wrist cuff is positioned adjacent to the wearer's wrist; and a generally resilient, flexible pad disposed on said glove front and elongated in the lengthwise direction thereof, said pad having a first end disposed proximate the center of said palm covering portion which extends substantially across said palm covering portion and which has a forwardly converging, tapering shape, said glove front being free of padding forward of said first end, said pad further having a second, substantially straight end disposed substantially at said wrist cuff.

4. The glove of claim 3, wherein said pad has a generally rectangular rear portion adjoining said wrist cuff which includes said second end, said pad further having a pair of parallel sides and a front portion including said first end overlying the center of said palm covering portion, said first end being rounded and connected with said parallel sides.

5. The glove of claim 4, wherein said pad is made of a foam rubber material.

6. The glove of claim 5, wherein said foam rubber is selected from the group consisting of neoprene, ethylene propylene terpolymer, styrene butadiene, and combinations thereof.

7. The glove of claim 3, wherein said pad is made of an elastomeric material having a compression deflection of at least 5 psi, a durometer of at least 40, a density of at least 5 pcf, and a resilience of at least about 25 based on a Bashore percent rebound average for 0.5 inch thickness at 72° F.

8. The glove of claim 4, wherein said second end of said pad has a width in the range of about one-half to two-thirds the corresponding width of said wrist cuff of said glove body when said glove is laid flat.

9. The glove of claim 8, wherein said pad has a length in the range of from about to 50% to 90% of the corresponding length of said glove front.

10. A glove effective for inhibiting carpal tunnel syndrome in the hand of a wearer who grasps and uses an implement with the hand on which said glove is worn, comprising:

a flexible glove body, including a glove front, a wrist cuff, a thumb portion, a palm heel portion, a palm covering portion disposed forwardly of said wrist cuff between said thumb portion and said palm heel portion, and a glove back secured to said glove front at the periphery thereof, said glove front and said glove back terminating at said wrist cuff, said wrist cuff defining a rear wrist opening into said glove body, a front opening at a forwardmost end of said palm covering portion, and a side thumb opening at said thumb portion, said wrist cuff being located adjacent the wrist of a wearer when said glove is disposed over the hand of the wearer; and a generally resilient, flexible pad disposed on said palm covering portion of said glove front, said pad being elongated in the lengthwise direction of said glove, said pad having a first end disposed proximate the center of said palm covering portion and a second end disposed proximate said wrist cuff, said glove front being free of padding between said first end and said front opening, said pad having a pair of generally parallel sides, respectively adjoining said palm heel portion and said thumb portion, said first end extending arcuately over said palm covering portion and connection said parallel sides.

11. The glove of claim 10, wherein said first end of said pad is substantially semi-circular.

12. The glove of claim 10, wherein a front portion of said pad bounded by said first end has a greater maximum width than the width of said pad between said parallel sides thereof.

13. The glove of claim 10, wherein said second end of said pad is straight and contiguous with said wrist cuff.

14. The glove of claim 10, further comprising means adjoining said cuff for releasably securing said glove on a wearer's hand.

15. The glove of claim 10 wherein said glove body is essentially free of finger and thumb coverings.

16. The glove of claim 10, wherein said glove body further comprises a series of spaced apart finger loops each attached at opposite ends thereof to said glove front and said glove back to subdivide said front opening into a series of finger openings.

17. The glove of claim 16, wherein said glove back includes an elastic panel.

18. The glove of claim 17, further comprising a releasable contact fastener disposed proximate said wrist for securing said glove to the hand of a wearer.

19. The glove of claim 10, further comprising a pair of elastic fabric liners disposed on opposite sides of said pad, and a seam disposed generally around the periphery of said pad securing said pad and said liners to said glove front.

* * * * *